US00PP25828P3

(12) United States Plant Patent
Bradford

(10) Patent No.: US PP25,828 P3
(45) Date of Patent: Aug. 25, 2015

(54) NECTARINE TREE NAMED 'PEARLICIOUS XVI'

(50) Latin Name: *Prunus persica*
Varietal Denomination: Pearlicious XVI

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 20 days.

(21) Appl. No.: 13/998,856

(22) Filed: Dec. 16, 2013

(65) Prior Publication Data

US 2015/0173273 P1 Jun. 18, 2015

(51) Int. Cl.
*A01H 5/08* (2006.01)

(52) U.S. Cl.
USPC ..... Plt./188

(58) Field of Classification Search
USPC ..... Plt./187, 188
See application file for complete search history.

(56) References Cited

U.S. PATENT DOCUMENTS

PP11,695 P 12/2000 Bradford et al.
PP18,696 P2 4/2008 Bradford

*Primary Examiner* — Susan McCormick Ewoldt

(57) ABSTRACT

The present invention relates to a new and distinct variety of nectarine tree, *Prunus persica*, broadly characterized by a small size, moderately vigorous, hardy, self-fertile, productive and regular bearing tree. The variety has large blossoms and blooms in the mid season, requiring about 550 chilling hours. The leaves are large and have globose glands. The fruit matures under the ecological conditions described in mid August, with first picking on Aug. 10, 2013. The fruit is large in size, globose in shape, clingstone in type, firm and melting in texture, white in flesh color, mostly red in skin color, and very sweet in flavor, and the kernel has a bitter taste.

1 Drawing Sheet

Botanical classification: *Prunus persica.*
Variety denomination: 'Pearlicious XVI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of nectarine tree, which has been denominated varietally as 'Pearlicious XVI'.

In the flowering season of 2003 I hybridized a first generation cross using 'Regal Pearl' (U.S. Plant Pat. No. 11,695) white flesh clingstone nectarine as the selected seed parent and an unnamed yellow flesh peach as the selected pollen parent. The fruit of this cross was gathered in the summer of 2003, and the seeds were removed from the fruit, germinated, stratified, and grown as seedlings on their own root in my greenhouse. Upon reaching dormancy the following winter, the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Regal Pearl' (U.S. Plant Pat. No. 11,695) nectarine by having a having globose leaf glands, by having a large blossom, being self-fertile, and producing white flesh clingstone nectarines that are firm, that are mostly red in skin color, that have a bitter kernel, and mature in mid August, but is distinguished therefrom by having globose instead of reniform leaf glands and by producing fruit that is much larger in size and is somewhat sweeter.

The present variety is most similar to 'Snow Pearl' (U.S. Plant Pat. No. 18,696) nectarine by having globose leaf glands, by having a large blossom that blooms in the mid season, by requiring about 550 chilling hours, by being self-fertile, and by producing white flesh clingstone nectarines that are firm and mostly red in skin color, but is distinguished therefrom by producing fruit that is larger in size, that matures about seven days earlier, that is sweeter, and that has a bitter kernel instead of sweet.

SUMMARY OF VARIETY

In summary, the present nectarine variety is characterized by a small size, moderately vigorous, hardy, self-fertile, productive and regular bearing tree. The variety has large blossoms and blooms in the mid season, requiring about 550 chilling hours. The leaves are large and have globose glands. The fruit matures under the ecological conditions described in mid August, with first picking on Aug. 10, 2013. The fruit is large in size, globose in shape, clingstone in type, firm and melting in texture, white in flesh color, mostly red in skin color, and very sweet in flavor, and it has a bitter kernel.

DRAWING

The accompanying photograph consists of four whole fruits positioned to display the characteristics of the skin color and form, one divided fruit to reveal the flesh and stone, three insets to reveal buds and blossoms, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of full ripe on Aug. 20, 2013, on the original tree during its tenth growing season. The blossom and flower descriptions were made the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: 'Regal Pearl' (U.S. Plant Pat. No. 11,695).
Pollen parent: Unnamed yellow flesh peach (unpatented).

TREE

Size: Small, reaching and maintaining a height of 7' [2.13 m.] and a spread of 6' [1.83 m.] after ten growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 550 hours.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

- *Size.*—Medium, reaching a maximum diameter of 3" [76.2 mm.] after the tenth growing season.
- *Texture.*—Medium shaggy.
- *Bark color.*—A Grayish brown [61. gy.Br] and Light grayish brown [60. l.gy.Br] variegation.
- *Lenticels.*—Approximate Number Per Square Inch: 8 to 10. Color: Strong brown [55. s.Br]. Average Size: ⅛" [3.2 mm.]. Shape: Eye-shaped, elongated.

Branches:

- *Size.*—Diameter of main scaffold is 2" [50.8 mm.] measured 12" above the crotch, Diameter of limb is 1¼" [31.8 mm.] measured 12" above the first fork.
- *Texture.*—Smooth on first year wood, increasing roughness with age.
- *Color.*—Second Year Wood: A Moderate yellowish brown [77. m.yBr] and Grayish yellowish brown [80. gy.yBr] variegation.
- *Lenticels.*—Number Per Square Inch: About 50 on second year wood. Color: Light yellowish brown [76. l.yBr]. Size: 1/64" [0.4 mm.] to 1/16" [1.6 mm.] on second year wood. Shape: Eye-shaped, elongated.

Leaves:

- *Size.*—Large. Average Length: 6½" [165.1 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Rounded.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: 7/16" [11.1 mm.]. Average Thickness: 1/16" [1.6 mm.]. Color: Brilliant yellow green [116. brill.YG].
- *Stipules.*—Number: Usually 2 per leaf, up to 6 per growing tip. Average Length: ⅜" [9.5 mm.]. Color: Light yellow green [119. l.YG] becoming Grayish brown [61. gy.Br] with maturity.
- *Glands.*—Number: 2 to 4 per leaf. Position: Mostly alternate with a few opposite, positioned on petiole and base of blade. Size: Medium. Form: Globose. Color: Brilliant yellow green [116. brill.YG] becoming Dark grayish brown [62. d.gy.Br] in the center with age.
- *Leaf buds.*—Pointed, medium in size.

Flower buds:

- *Hardiness.*—Hardy, with respect to central California winters.
- *Diameter.*—Typically 5/16" [7.9 mm.] 1 week before bloom.
- *Length.*—Typically ⅝" [15.9 mm.] 1 week before bloom.
- *Form.*—Not appressed.
- *Surface.*—Pubescent.
- *Tip color.*—Moderate purplish pink [250. m.pPk].

Flowers: Perfect, complete, perigynous, usually a single pistil, about thirty stamens, five sepal and petal locations alternately positioned.

- *Type.*—Showy, large.
- *Average flower diameter.*—2" [50.8 mm.].
- *Number of petals.*—Usually five, extra petal fragments commonly occur, double blossoms rarely observed.
- *Petal shape.*—Circular to oval.
- *Petal margin.*—Entire, somewhat wavy, occasional notches.
- *Average petal diameter.*—⅞" [22.2 mm.].
- *Average petal length.*—13/16" [20.6 mm.].
- *Petal apex.*—Rounded.
- *Petal base.*—Rounded to somewhat truncate.
- *Petal color.*—Moderate pink [5. m.Pk] toward the apex, Strong purplish pink [247. s.pPk] toward the base on both sides.
- *Anther color.*—Moderate red [15. m.R] over a Pale yellow [89. p.Y] center at bloom onset.

*Stigma color.*—Pale greenish yellow [104. p.gY].
*Average pistil length.*—13/16" [20.6 mm.].
*Average stamen length.*—11/16" [17.5 mm.].
*Sepal color.*—Dark purplish red [259. d.pR] on the outer surface.
*Sepal length.*—¼" [6.4 mm.].
*Sepal width.*—3/16" [4.8 mm.].
*Sepal apex.*—Rounded to elliptical to match the sepal length and width.
*Fragrance.*—Moderate.
*Blooming period.*—Medium, 2 days after 'Spring Bright' (U.S. Plant Pat. No. 7,507) nectarine.
*Onset of bloom.*—One percent on Mar. 6, 2013.
*Date of full bloom.*—Mar. 14, 2012.
*Duration of bloom.*—One to two weeks, dependent on ambient temperature.
*Number per cluster.*—1 to 3 with single flowers most common.

FRUIT

Maturity when described: Full ripe, Aug. 20, 2013.
Date of first picking: Aug. 10, 2013.
Date of last picking: Aug. 20, 2013.
Size: Somewhat variable, large.
*Average diameter axially.*—3⅛" [79.4 mm.].
*Average diameter across cheek plane.*—2⅞" [73 mm.].
*Average diameter across suture plane.*—3" [76.2 mm.].
*Typical weight.*—9.8 ounces [278 grams].
Form: Uniform, globose.
*Longitudinal section form.*—Round to oval.
*Transverse section through diameter.*—Round.
Suture: Extends from the base, continues along the side, to just past the pistil point.
*Near the base.*—A sharp groove.
*Along the side.*—A shallow trough.
*Near the apex.*—A sharp groove.
Ventral surface: Rounded, lipped toward the apex on both sides.
Lips: Slightly unequal.
Cavity: Flaring, elongated in the suture plane, suture showing on one side, Yellowish white [92. yWhite] stem markings typical.
*Depth.*—1¼" [31.8 mm.].
*Breadth.*—¾" [19.1 mm.].
Base: Truncate.
Apex: Rounded.
Pistil point: Oblique, mostly depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in a dry season.
*Color.*—Very deep red [14. v.deep R] over a Dark pink [6. d.Pk] background with some Pale yellow [89. p.Y] areas where protected from the son. Moderate Pale orange yellow [73. p.OY] freckling toward the apex.
Flesh:
*Color.*—Pinkish white [9. pkWhite] with Deep red [13. deep R] streaking next to the stone.
*Surface of pit cavity.*—Covered with Very dark red [17. v.d.R] broken fibers when twisted from the stone.
*Amygdalin.*—Scarce.
*Juice.*—Abundant, rich.
*Texture.*—Firm, crisp, meaty.
*Fibers.*—Abundant, fine.
*Ripens.*—Slightly earlier at the apex.
*Flavor.*—A sweet subacid, typically 20 to 22 brix.
*Aroma.*—Very slight.
*Eating quality.*—Excellent.

STONE

Type: Clingstone.
Form: Oval.
Hilum: Narrow.
Base: Rounded.
Apex: Acute.
Sides: Equal.
Surface: Irregularly furrowed near the apex, pitted toward the base.
Ridges: Jagged.
External color: Deep reddish brown [41. deep rBr].
Pit wall color when cracked: Moderate brown [58. m.Br].
Cavity surface color: Brownish orange [54. brO].
Average pit wall thickness.—5/16" [7.9 mm.].
Average width.—1¼" [31.8 mm.].
Average length.—1¾" [44.5 mm.].
Average breadth.—13/16" [20.6 mm.].
Tendency to split: None observed.
Kernel:
*Form.*—Oval.
*Skin color.*—Strong yellowish brown [74. s.yBr] when first removed.
*Pellicle color.*—Dark grayish yellowish brown [81. d.gy.yBr].
*Vein color.*—Dark grayish yellowish brown [81. d.gy.yBr].
*Taste.*—Bitter.
*Viable.*—Yes.
*Average width.*—9/16" [14.3 mm.].
*Average length.*—⅛" [3.2 mm.].
*Amygdalin.*—Abundant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Snow Pearl' (U.S. Plant Pat. No. 14,695) nectarine by having globose leaf glands, by having a large blossom that blooms in the mid season, by requiring about 550 chilling hours, by being self-fertile, and by producing white flesh clingstone nectarines that are firm and mostly red in skin color, but is distinguished therefrom by producing fruit that is larger in size, that matures about seven days earlier, that is sweeter, and that has a bitter kernel instead of sweet.

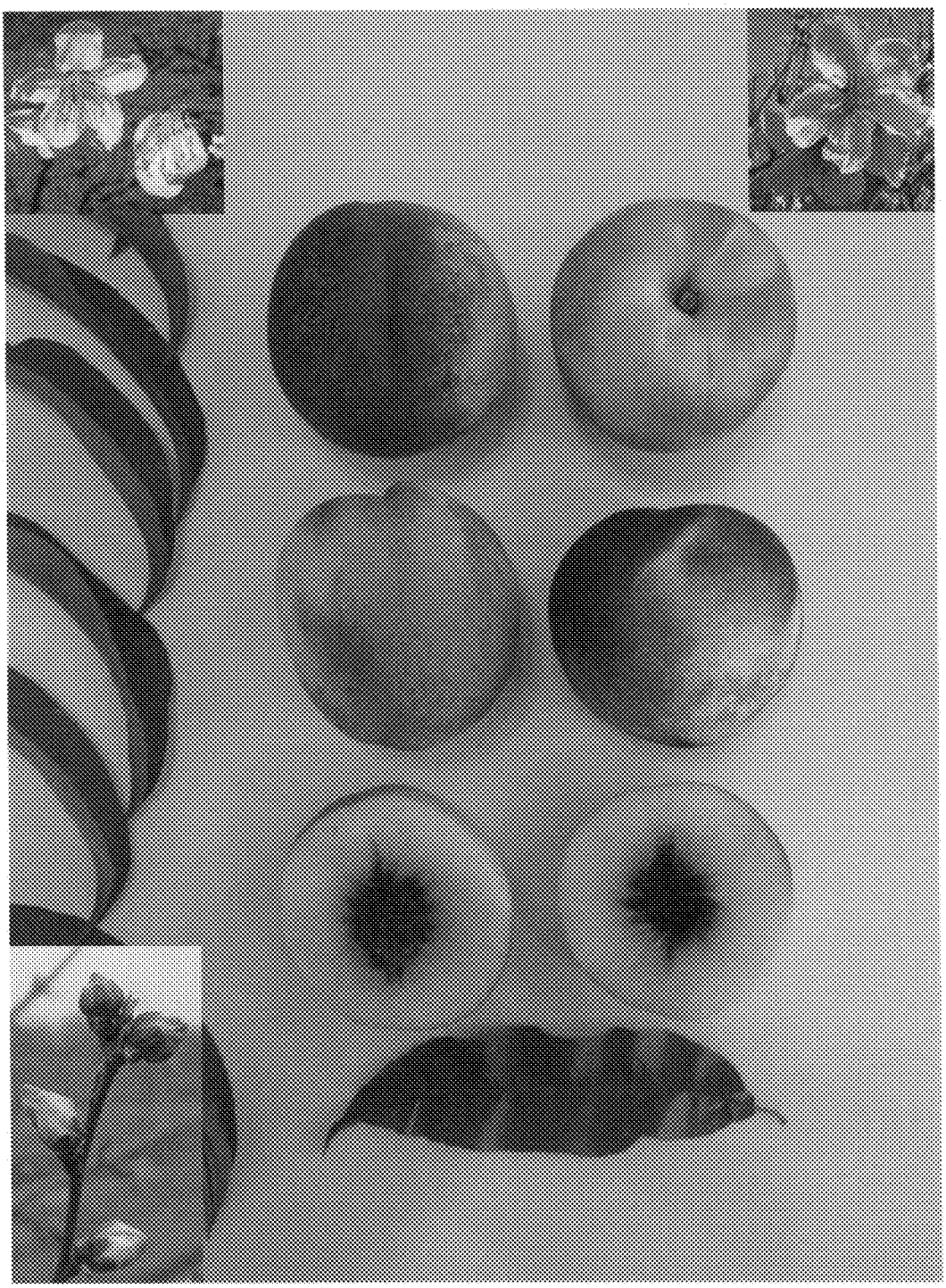

* * * * *